US009339228B2

(12) United States Patent
Saroka et al.

(10) Patent No.: US 9,339,228 B2
(45) Date of Patent: May 17, 2016

(54) ADJUSTABLE THORACIC GARMENTS USEABLE BY PATIENTS HAVING DIFFERENT THORACIC DIMENSIONS FOR LOCATING EM TRANSDUCER(S) IN PROXIMITY TO PREDEFINED THORACIC ANATOMIC FEATURES

(71) Applicant: Sensible Medical Innovations Ltd., Kfar Neter (IL)

(72) Inventors: Amir Saroka, Tel-Aviv (IL); Leonid Voshin, Kfar-Saba (IL); Ofer Karp, Haifa (IL); Shlomi Bergida, Udim (IL)

(73) Assignee: Sensible Medical Innovations Ltd., Kfar Neter (IL)

( * ) Notice: Subject to any disclaimer, the term of this patent is extended or adjusted under 35 U.S.C. 154(b) by 0 days.

(21) Appl. No.: 14/379,308

(22) PCT Filed: Dec. 18, 2013

(86) PCT No.: PCT/IL2013/051040
§ 371 (c)(1),
(2) Date: Aug. 18, 2014

(87) PCT Pub. No.: WO2014/097297
PCT Pub. Date: Jun. 26, 2014

(65) Prior Publication Data
US 2015/0031978 A1    Jan. 29, 2015

Related U.S. Application Data

(60) Provisional application No. 61/738,530, filed on Dec. 18, 2012, provisional application No. 61/738,412, filed on Dec. 18, 2012.

(51) Int. Cl.
| | | |
|---|---|---|
| *A61B 5/103* | (2006.01) | |
| *A61B 5/00* | (2006.01) | |
| *A61B 5/05* | (2006.01) | |
| *A61B 5/053* | (2006.01) | |
| *A61B 5/01* | (2006.01) | |
| *A61B 5/08* | (2006.01) | |

(52) U.S. Cl.
CPC ............. *A61B 5/6805* (2013.01); *A61B 5/0053* (2013.01); *A61B 5/05* (2013.01); *A61B 5/053* (2013.01); *A61B 5/01* (2013.01); *A61B 5/08* (2013.01)

(58) Field of Classification Search
CPC .... A61B 5/6805; A61B 5/053; A61B 5/0053; A61B 5/05; A61B 5/08
USPC ............................................ 600/546, 87, 595
See application file for complete search history.

(56) References Cited

U.S. PATENT DOCUMENTS

| 4,608,987 A | 9/1986 | Mills | |
|---|---|---|---|
| 2011/0184270 A1* | 7/2011 | Russell | .............. A61B 5/02055 600/388 |
| 2012/0144551 A1 | 6/2012 | Guldalian | |

FOREIGN PATENT DOCUMENTS

| JP | 06070897 A | * | 3/1994 |
|---|---|---|---|
| WO | WO 2011/117862 | | 9/2011 |
| WO | WO 2014/097297 | | 6/2014 |

OTHER PUBLICATIONS

International Preliminary Report on Patentability Dated Jul. 2, 2015 From the International Bureau of WIPO Re. Application No. PCT/IL2013/051040.
International Search Report and the Written Opinion Dated Apr. 7, 2014 From the International Searching Authority Re. Application No. PCT/IL2013/051040.

* cited by examiner

*Primary Examiner* — Max Hindenburg
*Assistant Examiner* — Jonathan M Foreman

(57) ABSTRACT

A thoracic garment for bringing an EM transducer to contact with a thoracic surface area of a wearer. The thoracic garment comprises a front thoracic garment piece and a back thoracic garment piece the front and/or back thoracic garment pieces having EM transducer(s), the front thoracic garment piece having an arrangement of passages formed therein or thereon, a handhold mechanically connected to the front thoracic garment piece, a positioning marker, and a plurality of straps each threaded in the arrangement of passages. The thoracic garment is configured to be adapted by the wearer which uses a first hand to hold the handhold for mounting the front thoracic garment piece against or close to the chest such that the positioning marker is positioned at the predefined position while using a second hand for pulling the straps.

20 Claims, 8 Drawing Sheets

ADJUSTABLE THORACIC GARMENTS USEABLE BY PATIENTS HAVING DIFFERENT THORACIC DIMENSIONS FOR LOCATING EM TRANSDUCER(S) IN PROXIMITY TO PREDEFINED THORACIC ANATOMIC FEATURES

RELATED APPLICATIONS

This application is a National Phase of PCT Patent Application No. PCT/IL2013/051040 having International filing date of Dec. 18, 2013, which claims the benefit of priority under 35 USC §119(e) of U.S. Provisional Patent Application Nos. 61/738,530 filed on Dec. 18, 2012 and 61/738,412 filed on Dec. 18, 2012. The contents of the above applications are all incorporated by reference as if fully set forth herein in their entirety.

FIELD AND BACKGROUND OF THE INVENTION

The present invention, in some embodiments thereof, relates to EM transducers positioning and, more particularly, but not exclusively, to a thoracic garment of positioning electromagnetic (EM) transducers and methods of using such a thoracic garment.

In various illnesses or situations, it is expedient to monitor a person or patient for diagnostic and therapeutic purposes. The monitoring may involve cardiac functions of respiration, skin resistance, transpiration, body temperature and the like. Depending on the type of illness or situation monitored, a mix of parameters is measured continuously over a period of more than a few minutes. This may require that sensors placed on the body would not significantly impair the comfort and the normal freedom of movement.

SUMMARY OF THE INVENTION

According to some embodiments of the present invention, there are provided a thoracic garment for bringing an EM transducer to contact with a thoracic surface area of a wearer. The thoracic garment comprises a front thoracic garment piece and a back thoracic garment piece at least one of the front and back thoracic garment pieces having at least one EM transducer or at least one mechanical connector for connecting the at least one EM transducer, the front thoracic garment piece having an arrangement of passages formed therein or thereon, a handhold mechanically connected to the front thoracic garment piece, a positioning marker located on or in the front thoracic garment piece such that when the thoracic garment is worn by a human wearer and the front thoracic garment piece is placed against or close to the chest of the human wearer, the positioning marker located in a predefined position in relation to one or more anatomical features of the wearer, and a plurality of straps each threaded in the arrangement of passages. The thoracic garment is configured to be adapted by the wearer using a first hand to hold the handhold for holding the front thoracic garment piece against or close to the chest such that the positioning marker is positioned at the predefined position while using a second hand for pulling the plurality of straps.

Optionally, an additional positioning marker is located on or in the back thoracic garment piece such that when the thoracic garment is worn by the human wearer and the back thoracic garment piece is placed against or close to the back of the human wearer, the additional positioning marker located in a predefined position in relation to one or more anatomical features of the wearer.

Optionally, at least one brake unit to lock the movement of each of the plurality of straps.

Optionally, further comprising at least one pulling element associated with each of the plurality of straps to pull the plurality of straps.

More optionally, the arrangement of passages is symmetrically arranged in or on the front thoracic garment piece so that the at least pulling element symmetrically pulls the plurality of straps along the left and right sides of the human wearer.

Optionally, wherein the positioning marker is integrated with the handhold.

Optionally, wherein when the garment is adapted by the wearer the handhold is located in a midway between armpits and below the bottom tip of the anatomical feature.

Optionally, wherein the anatomical feature is the jugular notch of the human wearer.

Optionally, wherein the front thoracic garment piece comprises a non-stretchable breast plate.

More optionally, the breast plate has the at least one EM transducer mounted thereon or therein.

Optionally, wherein the back thoracic garment piece comprises a non-stretchable back plate mechanically connected to at least some of the plurality of straps.

Optionally, wherein at least one of the front and back thoracic garment pieces has at least one mechanical connector for at least one EM transducer configured to detachably connect to the at least one EM transducer.

More optionally, each of the back thoracic garment piece and the front thoracic garment piece has an EM transducer or a mechanical connector for an EM transducer formed thereon. Optionally, wherein the back thoracic piece is mechanically connected to at least some of the plurality of straps, and wherein each of the plurality of straps passes in a mechanical communication with a pawl which allows continuous motion of a respective the strap in one direction while preventing motion in at least the opposite direction.

Optionally, wherein, wherein the pulling brings the thoracic garment back piece to a predetermined distance from the cervical vertebra C7 (vertebra prominens) of the wearer. More optionally, the neckline position is reached when a movement stopping structure is positioned in contact with the cervical vertebra C7 (vertebra prominens) of the wearer.

More optionally, the movement stopping structure prevents a movement of one of the plurality of straps when the EM transducer or mechanical connector for an EM transducer is positioned at a predetermined location with respect to a body part or organ of the wearer.

More optionally, the plurality of straps comprises shoulder straps which mechanically connect between the back thoracic garment piece and the front thoracic garment piece and mounted such that when the thoracic garment is worn by the human wearer and the front thoracic garment piece is placed against or close to the chest of the human wearer, the shoulder straps are laid over the left and right shoulders of the human wearer.

Optionally, the thoracic garment comprises left and right lateral straps which laterally and mechanically connected between the back thoracic garment piece and the front thoracic garment piece when fastened and mounted such that when the thoracic garment is worn by the human wearer and the front thoracic garment piece is placed against or close to the chest of the human wearer, the left and right lateral straps are laid over the underarm region of the human wearer.

Optionally, the arrangement of passages comprises an arrangement of channels.

Optionally, the thoracic garment comprises a pressure applying element associated with the thoracic garment for applying a pressure at least on the EM transducer when the thoracic garment is worn by the human wearer so that the EM transducer applies a respective pressure on a thoracic skin surface area of the wearer.

According to some embodiments of the present invention, there are provided a method of monitoring a dielectric related property of a thoracic tissue. The method comprises instructing a wearer of an electromagnetic (EM) transducer thoracic garment with at least one EM transducer to don the thoracic garment and place a positioning marker located on the EM transducer thoracic garment in relation to one or more anatomic feature(s) on his thorax or adjacent thereto, instructing the wearer to hold the EM transducer thoracic garment in place by using a handhold on the garment, while pulling at least one strap of a strap based mechanism which is mechanically connected to the thoracic garment to secure the at least one EM transducer to at least one location in proximity to at least one anterior or posterior thoracic skin surface area of the wearer, transmitting EM energy by the at least one EM transducer, and analyzing the EM energy to identify a dielectric related property of at least one thoracic tissue of the wearer.

The present invention provides one or more EM sensors enhanced garment with easy to use strap adjustment mechanism and a handhold. This garment is set to be donned by a wearer without assistance, allowing him to locate the one or more EM sensors in predetermined position, for instance location and/or rotational variances, also referred to herein as orientation, in relation to an anatomical feature. The garment is not custom made for the wearer but rather adapted to be worn by wearers having different bodily sizes and/or shapes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
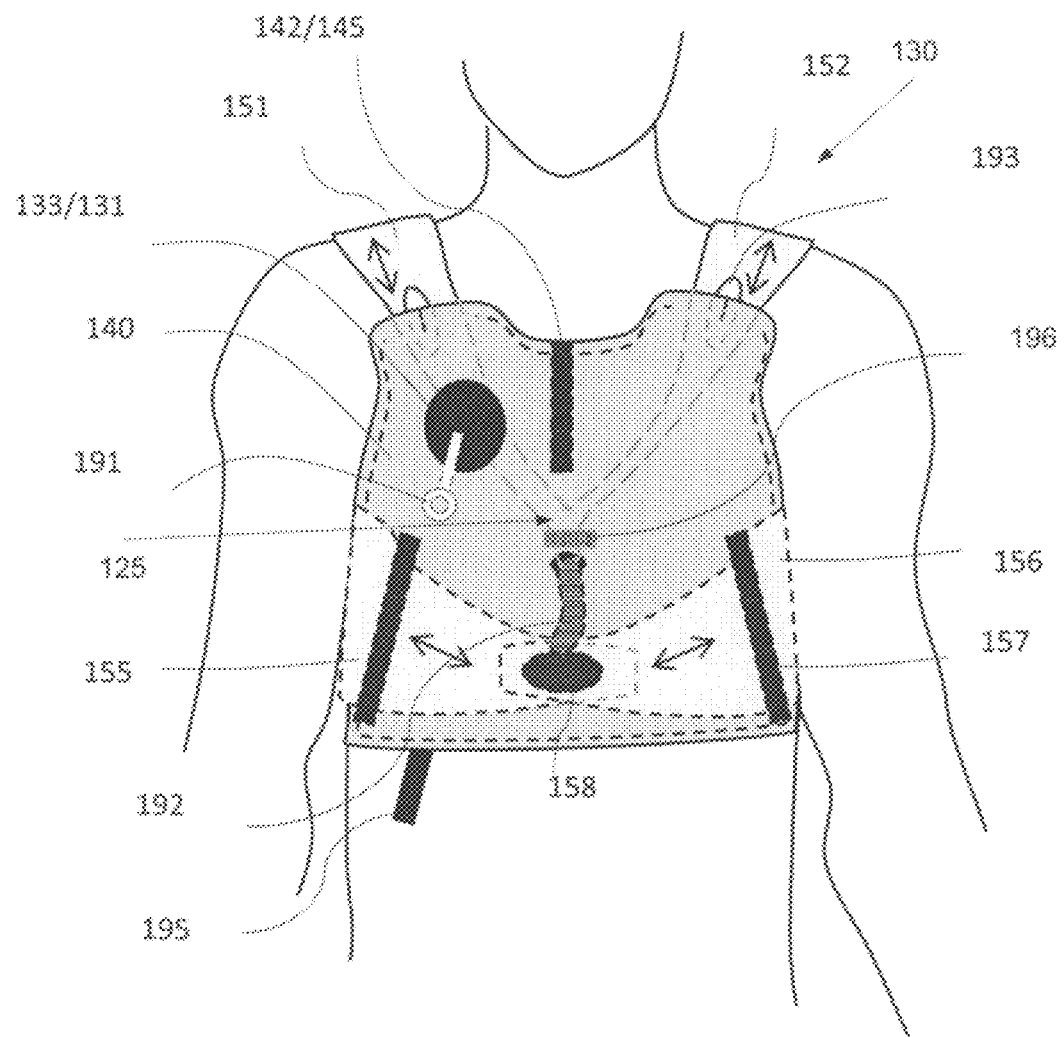
FIGS. 1A and 1B are anterior and posterior schematic illustrations of an exemplary thoracic garment, adapted to be worn with ease, optionally without the assistance of a caregiver, having a strap based mechanism for positioning one or more EM transducer units in a predefined location in relation to one or more anatomic features, according to some embodiments of the present invention.

The present invention, in some embodiments thereof, relates to EM transducers positioning and, more particularly, but not exclusively, to a thoracic garment of positioning electromagnetic (EM) transducers and methods of using such a thoracic garment.

According to some embodiments of the present invention, there is provided a thoracic garment having a strap mechanism that allows wearers having different bodily sizes and/or shapes to adjust the mounting of the thoracic garment such that EM transducers which are placed in or on the thoracic garment are located in a predefined orientation in relation to monitored anatomical tissues or organs. For example, the EM transducers are brought to be placed in front of the heart. The strap mechanism optionally includes a set of strap passages which is arranged such that when the straps which are threaded in the passages are pulled, the length of segments which connect between front and back pieces of the thoracic garment is optionally symmetrically and optionally simultaneously adjusted. The front piece of the thoracic garment optionally includes a handhold which allows the user to use one hand for orienting or positioning or positioning a positioning marker located on the thoracic garment in relation to one or more anatomic feature(s) and for holding the oriented thoracic garment in place and at same time to use the other hand for pulling one, some or all of the straps of the strap based mechanism.

It should be noted that according to some embodiments of the present invention, there is provided a garment with a single shoulder strap and/or with removable shoulder straps which allow removing one of the shoulder straps after an adjustment process wherein the length of the segments of the straps is adjusted by pulling.

According to some embodiments of the present invention, there is provided a method of wearing an EM transducer carrying thoracic garment by orienting or positioning a positioning marker located on the worn thoracic garment in relation to one or more anatomic feature(s) and firmly holding the oriented thoracic garment in place, while pulling one, some or all of the straps of a strap based mechanism that is mechanically connected to the thoracic garment. Optionally, the thoracic garment further includes lateral straps.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
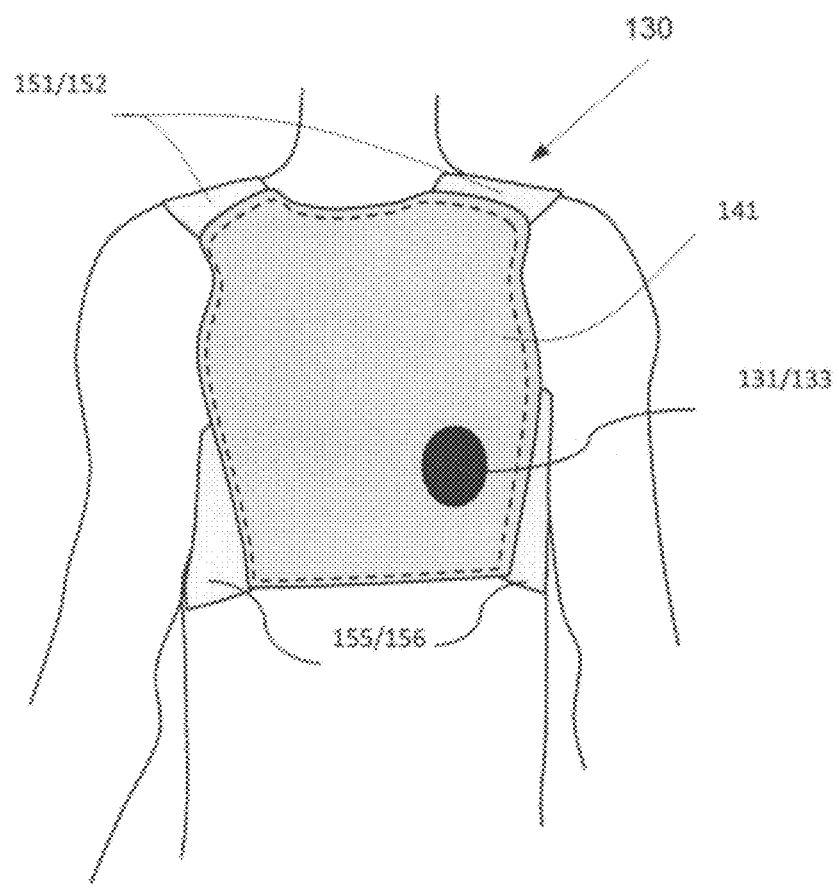

Reference is now made to FIGS. 1A and 1B, which are anterior and posterior schematic illustrations of an exemplary thoracic garment 130, adapted to be worn with ease, optionally without the assistance of a caregiver, having a strap based mechanism 125 for positioning one or more EM transducer units 133 in a predefined location in relation to one or more anatomic features, above one or more thoracic skin surface area(s), for example anterior and/or posterior thoracic skin surface(s) of a monitored wearer, according to some embodiments of the present invention.

The exemplary thoracic garment 130 is set to be donned by patients having different thoracic dimensions while bringing one or more of the EM transducer units 133 to a predefined orientation or position in relation to selected anatomical features. As used herein, the donned, worn, adjusted and adapted the exemplary thoracic garment 130 may be used interchangeably where donning and wearing may or may not include the adjustment or adapting, operations performed by adapting or adjusting the straps.

This allows using the thoracic garment 130 for monitoring changes in an intrabody tissue over a period of few minutes, hours, days or any intermediate or longer period with the option of re-orientating the EM transducer units 133 in different monitoring sessions in or about the exact location they have been in relation to one or more anatomical features. One exemplary thoracic garment 130 may also be replaced while maintaining the orientation or position of the respective EM transducer units 133.

The changes monitoring may be used for diagnostic, monitoring and therapeutic purposes. The thoracic garment 130 is set to place the EM transducer units 133 without an expert or a caregiver and therefore may be worn by an elder person at home without a caregiver. The thoracic garment 130 is set to place the EM transducer units 133 without significantly impairing the comfort and the normal freedom of movement of the wearer.

One or more EM transducers may be positioned by the thoracic garment 130 for use in transmitting and/or receiving EM energy that passes through the body or a portion thereof (e.g. a thorax) or organ or interest (e.g. lung), measuring biologically related dielectric properties of the wearer. The garment may comprise the one or more EM transducers and/or may comprise one or more mechanical connectors for connecting the one or more EM transducers to the garment. Thus the EM transducer(s) may be used in a row with a plurality of garments, for example where the garments are for single use or a single wearer over cloths.

Such measurements of dielectric related properties of the wearer may be analyzed (by a component of the garment and/or by a separate device) to provide data relating to biological properties of the wearer (e.g. fluid content) and/or a change in a biological property (for example between repeated measurements).

Optionally, in an initial state, the thoracic garment 130 is not fitted to a specific wearer and manually fitted by the wearer himself who uses one hand to pull straps of the strap based mechanism 125 and another hand for orienting or positioning a positioning marker 145 of the thoracic garment 130 in relation to one or more anatomic feature(s) and firmly holding the oriented thoracic garment 130 in place. Such a fitting brings the one or more EM transducers of the EM transducer units 133 to contact with one or more predetermined locations with the body of the wearer. The one or more anatomic feature(s) are optionally skeletal. An exemplary anatomic feature may be within 1 cm, 3 cm or 5 cm relative to a spinal bone, a certain rib and/or the sternum in one or two dimensions of the two dimensional plane of the skin.

The thoracic garment 130 may have one or more EM transducer placement portions 131, for example pockets, compartments, openings and/or attachments. Each EM transducer placement portion 131 is designed to host, for example to contain, at least one EM transducer unit 133. Optionally, the transducer unit 133, for example a unit comprising one or more EM transducers, is detachably connected to one or more mechanical connectors formed in the exemplary thoracic garment 130, for instance in a front thoracic garment piece 140 and/or a back thoracic garment piece 141 of the thoracic garment 130.

Additionally or alternatively, the thoracic garment 130 may have one or more permanently fixated transducer units 133. For example, EM transducer unit 133 may be integral in a garment or garment portion (e.g. sewn, glued or otherwise integrated in the portion). The EM transducer unit 133 is an EM transmission and/or reception unit which includes one or more EM transducer(s), comprising for example antennas with or without a housing and/or associated electronics, which are connected to an EM controller, for example circuitry which controls EM energy emission and/or processing.

The EM transducer placement portion 131 may be as defined in PCT Patent Application No. PCT/IL2012/050545 filed Dec. 20, 2012, which is incorporated herein by reference.

Optionally, the EM transducer unit 133 includes one or more pressure applying element which is associated with the thoracic garment, for example mechanically connected to the front thoracic garment piece 140 and/or the back thoracic garment piece 141. The pressure applying element applies a pressure on the EM transducer(s) of the respective unit 133 when the thoracic garment 130 is worn by the human wearer so that the EM transducer(s) apply a respective pressure on a thoracic skin surface area of said wearer. The pressure applying element is optionally as defined in PCT Patent Application No. PCT/IL2012/050545 filed Dec. 20, 2012, which is incorporated herein by reference. The pressure applying may cover more than the respective unit 133 or unit holding portion.

The thoracic garment 130 and/or any portion thereof may comprise and/or be set to support additional sensors for example for gathering data related to the physical condition of the monitored subject, for instance electrocardiogram (ECG) sensors, sensor, impedance sensor, acoustic sensor, temperature sensor, acidometer, acoustic sensors, accelerometer, and/ or the like. Optionally, any of the above sensors may be placed instead of the EM transducer unit(s) 133 described herein.

The thoracic garment 130 the EM transducer unit 133 and/or the EM transducer placement portions 131 are formed in and/or mounted on a front thoracic garment piece 140 and/or a back thoracic garment piece 141 of the thoracic garment 130. Each one of the thoracic garment pieces 140, 141 may be an elastic garment piece, for instance made of woven materials, rubber bands, and/or imitative synthetic fiber material with non elastic portions for the EM transducer units and/or with at least a non elastic backbone portion connected to the shoulder straps in each of the back thoracic garment piece 141.

Each one of the thoracic garment pieces 140 may be a non elastic garment piece, for example a non-stretchable breast plate having one or more EM transducers mounted thereon or therein. The non-stretchable breast plate may be made of a polymeric martial, polyvinyl chloride (PVC), metal and/or any non conductive material or low conductivity material that provides sufficient comfort and rigidity and/or be manufactured such that they will bend about a wearer's body and provides support to the EM transducer unit(s) 133 in the thoracic garment 130 and/or allows pressure to be applied to the EM transducer unit(s) 133 during operation; Examples for such EM transducers include one or more of the embodiments disclosed in PCT/IL2011/050003 filed Nov. 3, 2011, which is incorporated herein by reference in entirety. A garment plate may be regarded as rigid and/or non-elastic when it is sufficiently resistant to deformation and/or stretch-resistant to maintain the garment shape so that the EM transducer placement portions remains in place in relation to the thoracic skin surface areas during wearing and optionally also between at least 5 or at least 10 or at least 50 wearing sessions, each for a period of few minutes, hours, days or any intermediate or longer period. More optionally, one or more of the thoracic garment pieces 140, 141 has a 5 cm strip (or less) that would extend by no more than 1% 10%, 20%, or 60% of its length when attached to a load weighing 0.5 kilogram (Kg).

Optionally, the thoracic garment pieces 140, 141 or any strap thereof is made of or comprises EM manipulating materials. Optionally, EM manipulating materials may be positioned around the one or more positions of EM transducer units 133 in the thoracic garment 130. Optionally, EM manipulating materials are positioned between two or more positions of EM transducer units 133 in the thoracic garment 130.

The thoracic garment 130 further includes a handhold 142 which is mechanically connected to the front thoracic garment piece 140, for example being an integral part thereof. The handhold 142 allows the wearer of the thoracic garment 130 to mount the front thoracic garment piece 140 against or close to his chest such that a positioning marker 145 is positioned at a predefined orientation or position in relation to one or more anatomical feature of the wearer. The handhold 142 may be or comprise a loop, a handle, a knob, a slit in the garment, a rim of the garment (i.e. the rim of the neck opening itself) and/or any other hand gripping point that allows the wearer to firmly hold the front thoracic garment piece 140 against or close to his chest with one hand. The handhold may be a portion of a component of the garment having one or more additional functions (e.g. a protruding sensor), as long as it also provides a handhold. The handhold 142 may be positioned to be placed on top of the sternum in the middle of the thorax or between the shoulders, for instance midway between armpits.

The positioning marker 145 may be the handhold 142 itself or a part thereof and/or any visible or touchable positioning marker that is attached to, formed in and/or printed on the front thoracic garment piece 140, for example a hole, a transparent region, a marked dot, a triangle and/or a set of lines. The anatomical feature may be the jugular notch of the wearer. The anatomical feature may be in an area below the jugular notch of the wearer, for instance midway between armpits. The anatomical feature may be the sternum.

For example, in the exemplary thoracic garment 130 depicted in FIGS. 1A and 1B, handhold 142 is used as the positioning marker 145 which is set to be placed above the jugular notch.

The positioning marker 145 allows the wearer to position the front thoracic garment piece 140 such that the EM transducer unit(s) 133 (for brevity describing also EM transducer placement portion 131), of the thoracic garment 130 are positioned in proximity to target areas when the thoracic garment 130 is adapted and worn by the wearer. The EM transducer unit(s) 133 may be set to be located on the upper chest where no visibility is possible and the position marker 145 may be felt by the patient for locating it. Position marker 145 may have tips pointing toward the body which may be felt for self locating without visibility of the part. Optionally, the position marker 145 is placed on a segment that includes finger openings through which fingers of the wearer may be placed.

The strap based mechanism 125 includes a plurality of straps which are set to adjust the space between the front and back thoracic garment pieces 140, 141 and/or the position of the EM transducer unit(s) 133 in relation to the body of the wearer.

For example, the strap based mechanism 125 includes right and left shoulder straps 151, 152 set to be placed on top of the shoulders of the monitored wearer. Each of straps of the strap based mechanism 125, for instance 151, 152, is placed in a passage from arrangement of passages, for instance 153, 154. A passage may be form by rings, annular elements which are attached to any of the thoracic garment pieces 140, 141, a sleeve or a tube connected to any of the thoracic garment pieces 140, 141, a channel formed in any of the thoracic garment pieces 140, 141 and/or the like.

Optionally the two or more shoulder straps 151, 152 are inter-connected so that they may be adjusted symmetrically and simultaneously, for example by a single pulling maneuver, for instance as described below. In the shown example, the shoulder straps 151, 152 are both connected to a pulling band 192 that is mechanically connected to a pulling element 192 and/or to one to the other. Optionally the two or more shoulder straps are separate straps, or components of a single strap or strap arrangement that splits to form a plurality of straps, for example as shown in FIG. 1A. In this example, in order to adjust the length of the shoulder straps a wearer pulls on the pulling band 192 which serves as a pulling element. As the shared band moves downwards, the length of the exposed portions of the shoulder straps shortens and the back plate is pulled up along the wearer's back towards the neck, optionally bringing the top of the back garment piece 140 to contact with the wearer's vertebra prominens.

One or more pulling elements are associated with the strap based mechanism, for example one pulling element per strap or a central pulling element for pulling all the plurality of straps, for instance 151, 152. In the exemplary thoracic garment 130 a single pulling element shown here as pulling band 192 connects all straps, facilitating the pulling of the straps simultaneously. Optionally, the opposing straps are arranged in equally sized passages which are oriented symmetrically to the sides of a longitudinal axis traversing the thoracic garment 130, for example traversing a pulling element that is connected to both the right and left shoulder straps 151, 152. In such embodiments, pulling the pulling element shortens the length of segments of the right and left shoulder straps 151, 152 between the front and back thoracic garment pieces 140, 141 at a symmetric manner. For example, the pulling element may allow fitting both the shoulder straps by a single pulling action, for instance by pulling downwards a pulling band (e.g. 192) at a pulling element location to have a similar, if not identical, effect at both the right and left shoulder straps 151, 152 (depends on the symmetry of the shoulders of the wearer. In this example, pulling the pulling band 192 causes the two shoulder straps 151, 152 to pull the left and right sides of the back thoracic garment piece 140 at essentially the same rate.

The shoulder straps 151, 152, which may mechanically connect between the back thoracic garment piece 141 and the front thoracic garment piece 140 are mounted such that when the thoracic garment 130 is worn by the wearer and the front thoracic garment piece 140 is placed against or close to the chest of the wearer, the shoulder straps 151. 152 are laid over the left and right shoulders of the wearer, for example as depicted in FIGS. 1A-1B.

Optionally, the pulling element includes the shoulder strap band 192 that is connected to the right and left shoulder straps 151, 152 from one side. The shoulder strap band 192 may have teeth or any other set of projections therealong, optionally triangular. The shoulder strap band 192 is threaded via a unidirectional brake unit 196 which optionally includes slot and a flexible pawl arranged such that when the shoulder strap band 192 slopes in one direction, the triangular teeth interact with the flexible pawl that rides up the slope of these teeth when the shoulder strap band 192 is inserted, optionally irreversibly. The pawl engages the backside of these teeth to stop removal of the shoulder strap band 192. The unidirectional brake unit 196 may include any one way ratchet mechanism which allows continuous motion of the shoulder strap band 192 in one direction while preventing motion in the opposite direction. Optionally, a number of pulling elements are separately used to mechanically control the grasping and/or releasing of the straps. The unidirectional brake unit 196 optionally has a release mechanism which releases the hold on the band when being pressed, pulled, and/or slid.

The above thoracic garment 130 is to be donned by the wearer which uses one hand to hold the handhold 142 for mounting the front thoracic garment piece 140 against or close to the chest of the wearer such that the positioning marker 145 is positioned at a predefined orientation or position in relation to an anatomical feature and the other hand for to pull the pulling element 192. In such a manner, the thoracic garment 130 without a third party aid and/or any without supporting wearing mechanism.

Optionally, the shoulder straps 151, 152 pass via a unidirectional brake unit in contact with the shoulder straps or a band connected thereto. The unidirectional brake unit blocks the release of a stretched strap, for example when placed as a shoulder strap fastener. Optionally, the unidirectional brake unit allows the pulling band 192 to move solely in a downwards direction. The unidirectional brake unit may not allow repeated use of the straps. The unidirectional brake unit may comprise a slot through which the pulling band 192 passes. The pulling band 192 has a plurality of ridges that may pass solely in one direction through the slot as the ridges have a thicker backside than front side. Optionally, the shoulder straps 151, 152 are made of or comprise a two-way stretch fabric that allows the shoulder straps 151, 152 to stretch only in one direction.

Optionally, one or more shoulder straps 151, 152 are associated with an anchor arrangement, such as 193, so that the shoulder straps 151, 152 cannot be removed and/or adjusted more than by a predetermined length. In the instant example, the anchor arrangement 153 comprises an elongated opening in the shoulder strap 152 and a stopper, for example which connects two layers of the front thoracic garment piece 140, for instance a stitch connecting the two layers and encircled by the opening. This allows some motion of the strap 152 along the elongated opening however limits the motion to the length of the elongated opening, for example few centimeters (cm), for instance between about 1 cm and about 5 cm.

Optionally, lateral straps 155, 156 are set to connect between the front and back thoracic garment pieces 140, 141. Optionally, lateral strap holders, each such as 157, are added to fixate the length of the lateral straps 155, 156 to the front thoracic garment piece 140 after their length is set in manner that the front and back thoracic garment pieces 140, 141 are attached to the body of the wearer. Optionally, lateral straps fastener 158 is used to fixate the lateral straps 155, 156 to one another and optionally to the front thoracic garment piece 140. This may any fastener that may generally be used for fastening or attaching cloth parts to one another or to another material, including one or more buttons, buckles, belt buckles, hooks, hook-and-loop fastener (e.g. Velcro), zippers, tying straps, or any other type of connectors. The lateral straps 155, 156 tighten the thoracic garment 130 along the thorax laterally. In the example shown in FIGS. 1A-1B, lateral straps are sewn to the back thoracic garment piece 140 and adjustable along the front plate, under the armpits, at or above the waistline. Optionally, the lateral strap is fastened with a unidirectional arrangement, similarly to the zip tie example provided for the pulling band. Channels may also be used to define the movement of the lateral straps.

Optionally, the top edge of one or more of the lateral strap(s) is attached to the back plate at a high position such that when the garment is worn and tightened, and the top of the back plate touches the wearer's vertebra prominens, the respective strap is at a high underarm position, optionally in contact with the armpit or even applying some pressure on the arm at the armpit.

Optionally, the pulling of the straps 151, 152 is set to bring upper rim of the back thoracic garment pieces 140 to a neckline position, namely to a predetermined distance from the cervical vertebra C7 (vertebra prominens) of the wearer. For example, the top portion of the back thoracic garment pieces 140 may include a recess curved for engulfing the back of the neck of the wearer. Optionally this upper rim is part of the back plate.

Optionally, the pulling of the straps 151, 152 is set to bring upper rim of the back thoracic garment pieces 140 to contact with the cervical vertebra C7 (vertebra prominens) of the wearer.

Optionally, the pulling element(s) irreversibly lock the straps in place, for example using one way ratchet mechanisms and/or the like. In such embodiments, the thoracic garment 130 may be set for a single use and/or a multiple use. Optionally, locking of the straps may be done in two directions so as not to lose fit when removed.

Such locking may be facilitated by an additional mechanism that includes buttons, knits, ties, and breaking of remaining straps.

Figure 1C:
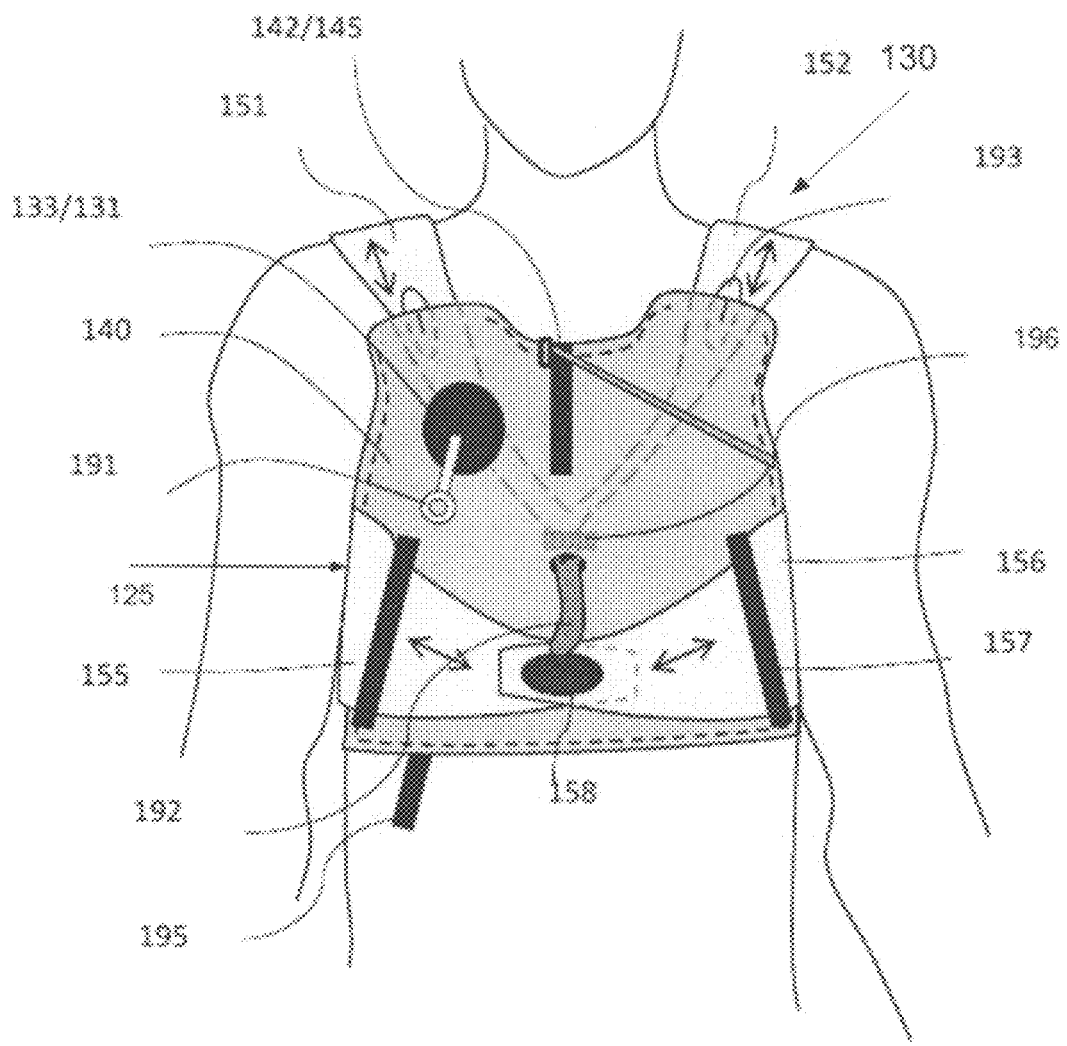
FIGS. 1C and 1D are anterior and posterior schematic illustrations of an exemplary thoracic garment with a fastener for temporal removal of the exemplary thoracic garment depicted in FIGS. 1A and 1B between monitoring sessions, according to some embodiments of the present invention.
Figure 1D:
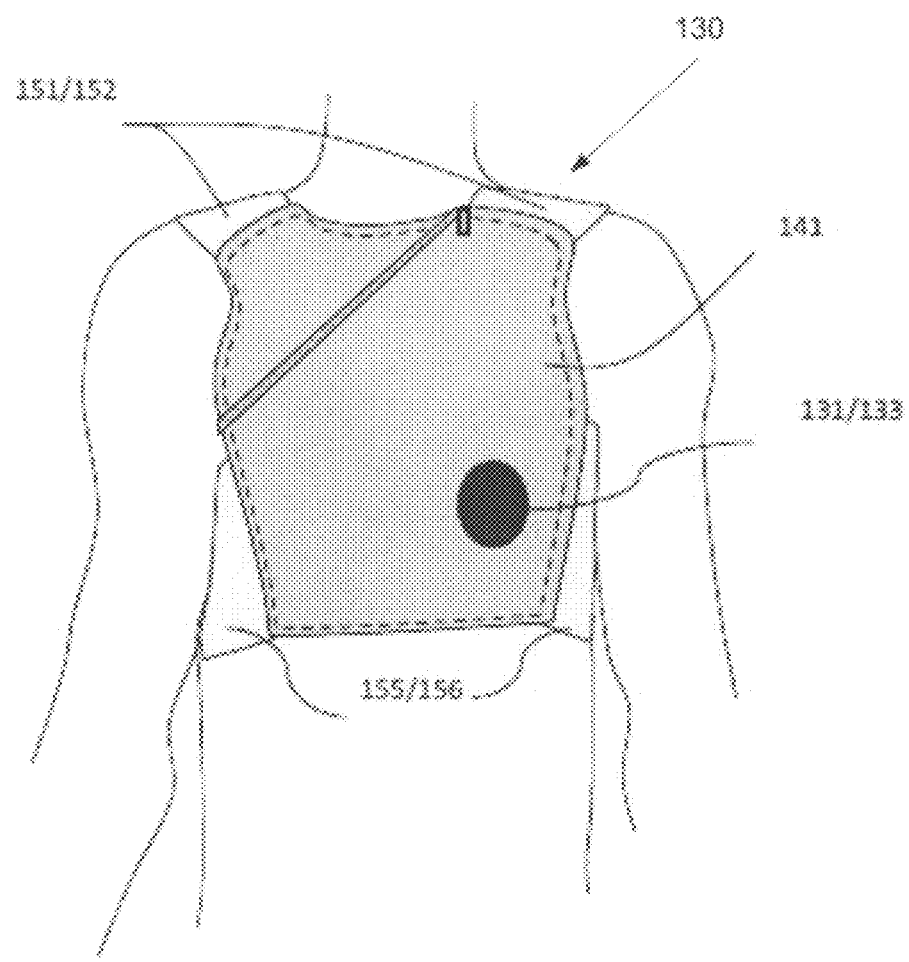

When the thoracic garment 130 is set for multiple use a device for temporarily joining two edges of any of the thoracic garment pieces 140, for example one or more buttons, buckles, belt buckles, hooks, hook-and-loop fastener (e.g. Velcro), zippers, tying straps, or any other type of connectors which may be used for wearing or taking of the and thoracic garment 130 in multiple sessions. For example FIGS. 1C and 1D are anterior and posterior schematic illustrations of an exemplary thoracic garment with fasteners 219, 218 for temporal removal of the exemplary thoracic garment depicted in FIGS. 1A and 1B between monitoring sessions, according to some embodiments of the present invention. In this example, the fasteners 219, 218 are zippers connecting parts of the front and back thoracic garment pieces 140, 141. In another example, one or two of the shoulder straps 151, 152 may be removable. In such embodiments, the straps are stretched and fixated during the first wearing event, forming a thoracic garment sized and/or shaped according to the specific dimensions of the wearer such that EM transducer(s) are brought to be in front of predefined anatomical features of the wearer.

Then, the wearer may take the thoracic garment 130 off and on using the device for temporarily joining two edges of any of the thoracic garment pieces 140, leaving the straps fixated between and during a number of iterative wearing periods. Such a thoracic garment 130 may be repeatability worn by the wearer repeatability bringing the EM transducer unit(s) 133 to a desired location as described above. In experiments done using the exemplary thoracic garment 130 depicted in FIGS. 1A and 1B, the repeated positioning of the EM transducer unit(s) was measured within a maximal distance of about ±25 millimeters (mm) for more than 68% of the repositioning attempts which are within aforementioned distance. In fact, it was experimentally shown that the EM transducer was placed within ±2 cm from the predetermined location above the skin of the wearer for at least 50% of repeat wearing sessions without refitting, and even within ±10 mm for at least 68% of the repeat wearing sessions. In fact, for an EM transducer unit placed within the anterior thoracic portion repositioning was obtained within ±5 mm for at least 68% of the repeat wearing sessions and for an EM transducer unit placed within the posterior thoracic portion repositioning was obtained within ±7 mm for at least 68% of the repeat wearing session. As used herein, when the terms repeatable and repeatability are used with reference to placement, positioning and/or return to a position of an element, such as an EM transducer and/or a garment portion, they mean that the process is repeated with high precision of positioning so that the repeated positions of the element are close one to the other and/or with high accuracy of positioning so that the repeated positions of the element are close to a predetermined value.

Additionally or alternatively, the thoracic garment 130 may be disposable in its entirety or comprise a disposable fabric portions, for example lining set to be placed at the back of any of the thoracic garment pieces. In another example, the front and/or back thoracic garment pieces 140, 141 are set to be detachably connected to the strap based mechanism 125, facilitating the replacement of one thoracic garment piece with another while maintaining the strap based mechanism 125. Optionally, one or more of the electronic components, such as EM transducer unit(s) 133, may be separated from the thoracic garment 130 making the front and/or back thoracic garment pieces 140, 141 and/or the strap based mechanism 125 disposable. The detached electronic components may be reused with another garment and/or shipped for analysis. Examples for such detachable elements are found in PCT Patent Application No. PCT/IL2012/050545 filed Dec. 20, 2012, which is incorporated herein by reference.

As described above, each EM transducer unit 133 may include a pressure applying element associated with the thoracic garment. For example, reference is now made to FIGS. 2A-2B which are lateral and top schematic illustrations of an exemplary EM transducer unit 100, according to some embodiments of the present invention, to FIG. 3 which is a lateral view of an alternative EM transducer unit, according to some embodiments of the present invention, and to FIGS. 4A and 4B which are schematic cross sections of an EM transducer unit having an inflatable pressure applying element, according to some embodiments of the present invention.

Figure 2A:
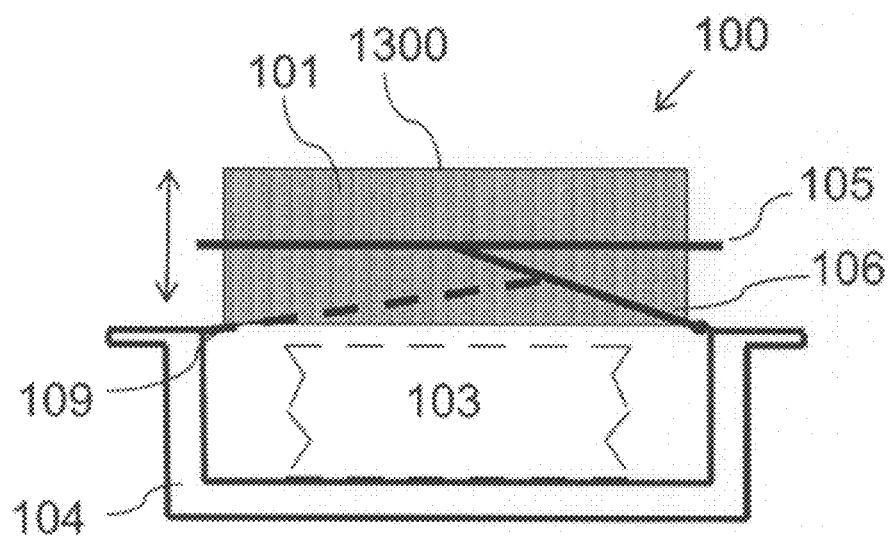
FIGS. 2A-2B are lateral and top schematic illustrations of an exemplary EM transducer unit, according to some embodiments of the present invention.

FIG. 2A depicts a lateral view of an exemplary EM transducer unit 100 having an EM transducer 101 with a frontal surface 1300 positioned slightly above an opening of a pressure applying element which includes a cup shaped housing 104 that functions as an anchoring mechanism. The cup shaped housing 104 is shown in an exemplary cross section, but may be shaped for example as a box, a cube, a dome, a cone and/or a pyramid. The housing 104 may comprise any durable and/or non-elastic enough and/or rigid enough material to provide support to EM transducer(s) 101 and to allow pressure to be applied to the EM transducer(s) during operation such that the frontal surface 1300 is displaced and move away from the bottom of the housing toward the thoracic skin surface area.

Optionally, the housing 104 is made of or at least partially coated with an EM manipulating material, for example an EM conductive or absorbing material. The pressure applying element further includes an extendable member 103 positioned in the housing 104 to push the EM transducer 101. Extendable member 103 may be for example a pneumatic linear actuator or an inflatable member that may be inflated by a fluid, be it liquid or gas. Extendible member 103 may include for example, under and/or around the EM transducer, a spring and/or a piston operated by a motor.

In use, the EM transducer unit 100 is positioned with the frontal surface 1300 facing a skin surface area of a wearer, the EM transducer unit 100 being secured to the body of the wearer by a garment as disclosed herein. The garment fixes the housing 104 such that upon extension of the extendible member 103, the EM transducer 101 moves in the direction of the wearer's body thereby coming to tight contact between the frontal surface 1300 and the skin surface of the wearer.

Figure 2B:
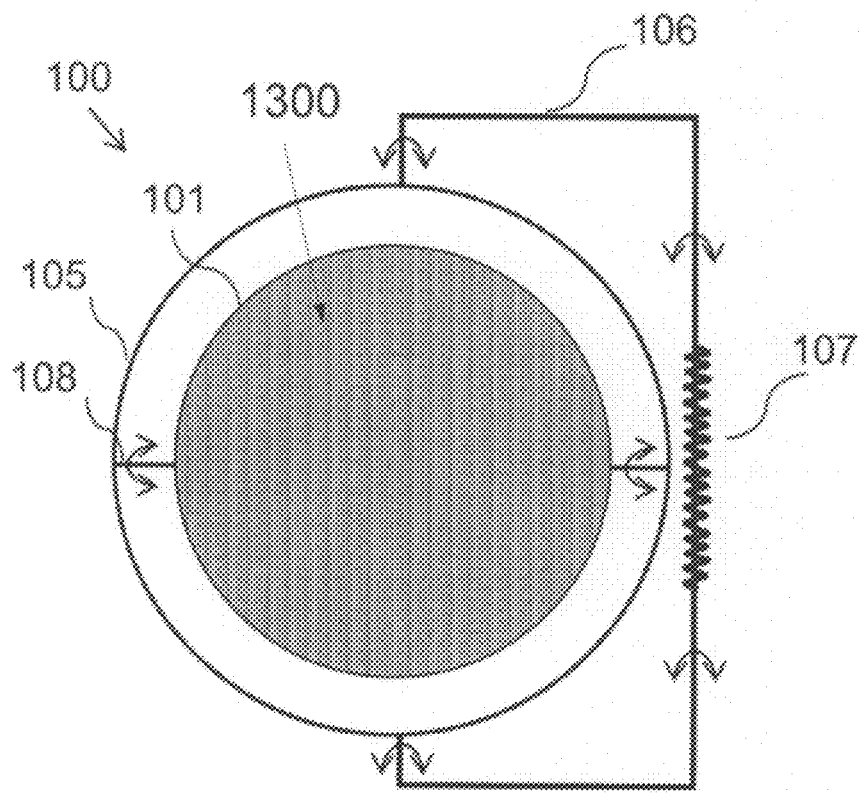

FIG. 2B depicts a top view of the EM transducer unit 100, showing an exemplary tilt mechanism having a gimbal arrangement (105, 106, also shown from lateral view in FIG. 2A) attached to an EM transducer 101. The gimbal arrangement ring 105 is connected to the EM transducer 101 by axel 108, allowing the EM transducer 101 to tilt around the axel. The gimbal arrangement ring 105 is attached to frame 106 such that the EM transducer 101 may rotate around the axis formed by the frame 106 where contacting the EM transducer 101.

As seen in FIG. 2A, frame 106 is hingedly connected to housing 104 such that the edge of the frame that is not attached to the housing may move upwards and allow EM transducer(s) 101 to move away from housing 104 as extendible element 103 extends. Optionally, arm 109 is hingedly connected to housing 104 through a first edge of the arm on one side and a second edge is slideably connected to frame 106. When EM transducer 101 is pushed away from housing 104, the second edge of arm 109 moves upwards, slides along an arm of frame 106 to move EM transducer 101 essentially vertically away from housing 104.

In some embodiments, the EM transducer 101 may be displaced vertically a distance of 2-6 cm or 3-5 cm. When extendible element 103 retracts, for example when it is deflated, EM transducer 101 is free to return into housing 104, for example by a counter pressure from the body of the wearer. This may be facilitated by exerting force in essentially the same direction, for example by spring 107.

Figure 3:
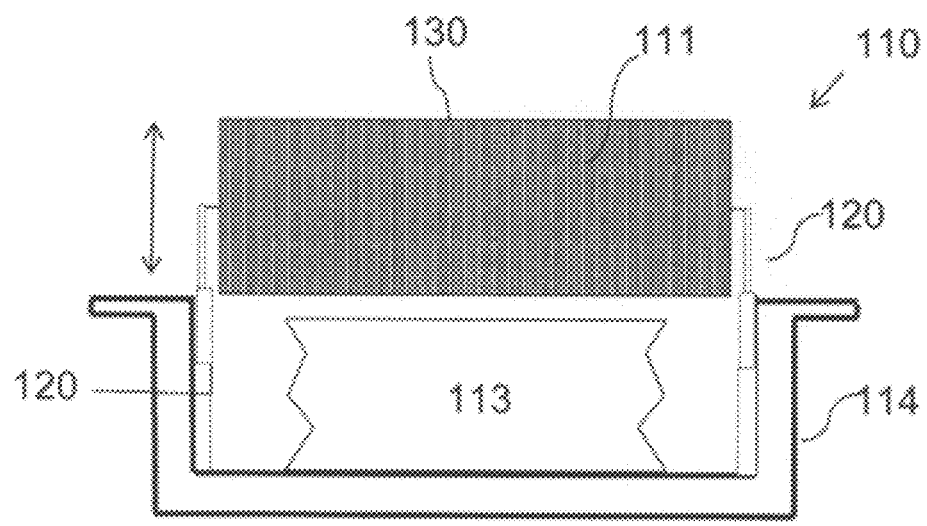
FIG. 3 is a lateral view of an alternative EM transducer unit, according to some embodiments of the present invention.

FIG. 3 depicts a lateral view of an alternative EM transducer unit 110 where an EM transducer 111 is held in housing 114 and pushed away from the bottom of the housing by an extendible element 113. In this example, the EM transducer 111 is anchored to the bottom of the housing 114 using a number of telescopic elements 120.

When the EM transducer 111 is pushed away from the housing 114, telescopic elements 120 extend, holding it in position during movement. Once extendible element 113 retracts telescopic elements 120 retract and allow the EM transducer 111 to move toward the bottom of the housing 114 or even pull it in this direction.

Figure 4A:
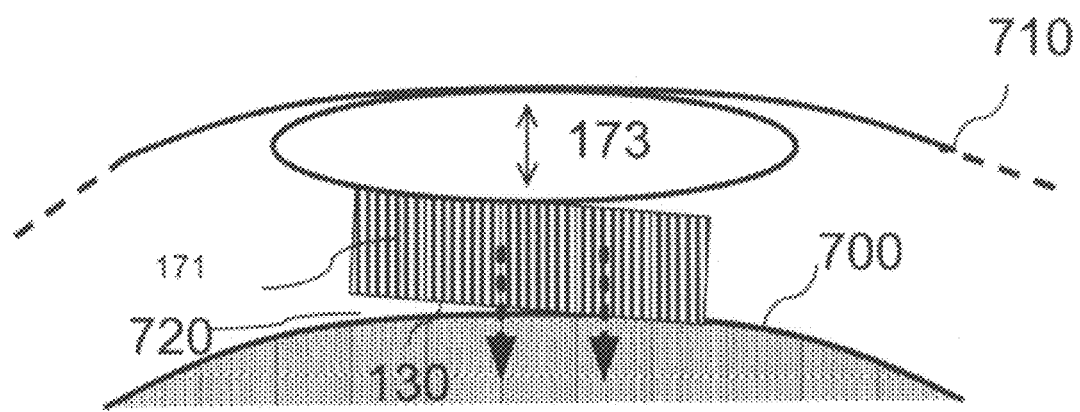
FIGS. 4A and 4B are schematic cross sections of an EM transducer unit having an inflatable pressure applying element, according to some embodiments of the present invention.
Figure 4B:
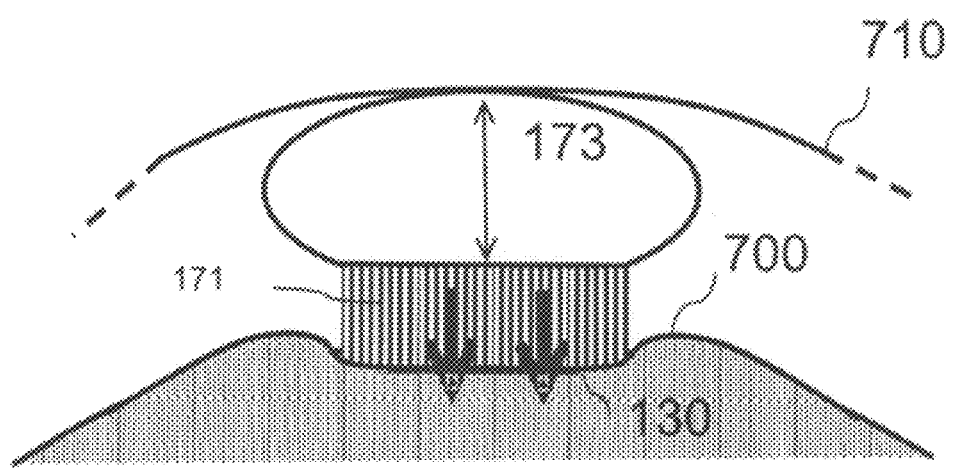

Reference is now made to FIGS. 4A and 4B which are schematic cross sections of an EM transducer unit 171, placed between a thoracic garment piece 710 and a wearer's body surface 700, directly or indirectly (for example above a piece of an undershirt or any other garment or fabric that is worn on the upper body or is a part of the garment), according to some embodiments of the present invention. In FIGS. 4A and 4B, the extendible member 173 is an inflatable element positioned between garment piece 710 and EM transducer 171 that is respectively depicted in partly deflated and inflated states. As used herein inflating and deflating are performed by flowing a fluid (liquid and/or gas). While the garment is fitted to some degree of tightness to the wearer and hence exerts a low pressure on body surface, for example a in the direction depicted by dashed arrows, it is loose enough to allow the EM transducer surface 1300 to tilt with respect to body surface 700. The tilt forms a gap 720 between EM transducer surface 1300 and the body surface 700. As extendible member 173 and the EM transducer 171 are sandwiched between a relatively non-elastic garment portion 710 and the wearer's body, extension of extendible member 103 caused EM transducer 171 to apply a higher degree of pressure on the wearer's body surface 700, depicted by bold line arrows in FIG. 4B. Since the wearer's body comprises pliable tissue(s) at the area shown, the body part compresses slightly under the pressure and surface 1300 of EM transducer 171 is brought to full surface contact with body surface 700. Such an arrangement as shown in FIGS. 4A and 4B (including an EM transducer unit 171 and extendible member 173) may in some embodiments be sewn into the garment, with a layer of material (e.g. a fabric or cloth) placed under EM transducer 171 (not shown).

Thus, when in use, the layer of material will come between EM transducer surface 1300 and the body surface 700.

Optionally, the above mentioned pressure controller (not shown) controls the degree of displacement of the EM transducer 101, 111 or 171 from within its housing or from its support (e.g. garment piece 710) and towards the body and/or the pressure exerted by the EM transducer(s) mechanism on the wearer and/or the pressure exerted on the EM transducer(s). The EM transducer surface 1300 may be pushed from a resting position in a housing and towards a wearer's body by 0.5 or more centimeters. For example, this may be between 0 cm and 7 cm or more, for example between 3 cm and 5 cm or more.

Optionally, the pressure level applied on the EM transducer 101, 111 or 171 may be between 100 millibar (mbar) and 600 mbar, for example between 200 mbar and 400 mbar or about 300 mbar within inflatable member 173 or and/or between 0.01 Kg/cm2 and 0.3 Kg/cm2 on the wearer's body. The degree of pressure may be set to be the same for a plurality of measurements to ensure repeatability of the pressure and/or comparability of measurements taken at different times. This may be controlled for example by a gauge, a pressure sensor, to provide feedback control for a pneumatic or hydraulic pump which pumps fluid into the inflatable member 173 or 113 or 103 and/or by use of a displacement sensor. Optionally, pressure may be controlled manually.

Optionally, the outcome of the gauge, a pressure and/or a displacement degree, is displayed to allow a manual pressure adjustment. Alternatively or additionally, it may be desired to take EM measurements at a plurality of different pressure/displacement settings.

Additional mechanisms may be used for retracting an EM transducer form a position where it applies pressure on a wearer's body. For example, in some embodiments, an EM transducer may be retracted by releasing pressure from an inflatable member 103, 113 or 173 and allowing for gravity and/or a retracting motion of the extendible member or a portion thereof to pull the EM transducer.

Additionally or alternatively one or more springs and/or elastic components that are attached, directly or indirectly to the EM transducer and an anchoring position can be used (for example spring 107 as described above). When an extendible member extends and displaces the EM transducer, the spring and/elastic components extend as well. Once the extendible member retracts or reduces the pressure applied on the EM transducer, the spring and/elastic components snap back to position, pulling the EM transducer with them.

In order to reduce the chance of the EM element displacing once an inflatable member is deflated (e.g. during undressing and/or redressing), a mechanism may be used to manually or automatically lock the EM transducer in place. This function may be provided at least partly, the aforementioned spring and/or elastic components.

Additionally or alternatively, to reduce unintentional inflation of an inflatable member (even if partial) a valve in the inflatable member that might allow fluid into the inflatable member is shut, thereby preventing fluid from flowing back into the inflatable member (e.g. air from the environment).

Optionally, the pulling element(s) 192 are optionally mechanically connected to the extendible member 103, for instance the inflatable member 103, 113 or 173 and/or to an interface of a controller which triggers the operation of the extendible member 103. In such embodiments pulling the pulling element(s) 192 triggers the pressure applying operation of the extendible member 103, for instance the inflatable member 103, 113 or 173. In such a manner, the wearer can both adjust straps and trigger the operation of the pressure applying unit with one or few hand gestures.

Optionally, the EM pressure applying element is set for multiple uses and/or for applying a controllable and/or varying degree of pressure on the EM transducer(s).

Optionally, the EM pressure applying element is configured for single use, thereby potentially reducing the weight and cost of a garment. For example—a spring arrangement which includes an extendible member, such as 103, may be released by pulling on an EM transducer band 191 connected to the pressure applying element, inducing the appliance of pressure on the EM transducer(s). In another example, gas is released by unsealing, optionally irreversibly, a pressured container for inflating the inflatable member 103, 113 or 173 to apply pressure on the EM transducer.

Optionally, the thoracic garment 130 comprises electronic and/or mechanical components for operating and/or controlling of the operation of EM transducer units 133. The electronic and/or mechanical components may be detachably attached to the thoracic garment 130. This is exemplified by a component connector 195 appearing at the bottom of the front plate in FIG. 1A.

As described above, according to some embodiments of the present invention, the thoracic garment pieces 140, 141 or any strap thereof is made of or comprises EM manipulating materials. As used herein, an EM manipulating material may mean a material that affects an EM wave and/or field propagation, for example by absorbing and/or dissipating energy, and/or by conducting, being resistive to, isolating, deflecting and/or attenuating EM energy. Examples for EM manipulating materials include EM energy absorptive materials and ferromagnetic materials and/or structures. In some examples the EM manipulating materials are in the form of or embedded in a fabric, for example a fabric comprising resistive fibers or ferromagnetic material comprising fibers. The EM manipulating materials are optionally layered, optionally set in sewed or otherwise connected in patches and/or intertwined and/or embedded in a fabric portion or a layer thereof. EM manipulating material(s) may be taken to mean materials including or consisting of one or more of EM absorptive and/or restrictive and/or conductive materials, and/or resistive sheet and/or fabric, and/or materials having significantly higher permittivity and permeability than air, and/or materials having permittivity and/or permeability with high loss, and/or a construction of materials (or metamaterials) with different impedance for guiding the radiation away from inside body and/or on the periphery of the body.

In some embodiments, EM manipulating materials comprise metamaterials.

Metamaterials may be structures or a combination of structures of metals or different materials with different permittivity and permeability with or without components with different inductance, reactance, and/or resistive properties integrated into them in a certain structure so as to implement desired impedance. It may comprise a network of resistors with capacitors and coils. Examples for EM manipulating materials include materials having one or more of the following properties:

Permeability loss tangent of (tan $\delta = \mu''/\mu'$)>0.01 or >0.3 or >0.6 for all or some of the frequencies within the range of 100 MHz-5 GHz for example for 1 GHz and/or 2 GHz.

Permittivity loss tangent of (tan $\delta = \in''/\in'$)>0.01 or >0.3 or >0.6 for all or some of the frequencies within the range of 100 MHz-5 GHz for example for 1 GHz and/or 2 GHz.

Partial conduciveness manifested by a surface resistivity between 20 and 10,000 Ohm per square ($\Omega$/sq) and/or a volumetric resistivity which is $>10^{-3}$ Ohm meter ($\Omega$m).

For example, resistive substrates and/or volumetric resistive materials may be constructed from and/or comprised of resistive wiring and/or conductive wires with or without lumped resistors, capacitors, and/or inductance elements.

Examples for EM manipulating materials include CobalTex™, which is a near field magnetic radio frequency (RF) shielding fabric of Less EMF Inc. or Eccosorb™ of Emerson and Cuming Microwave Products. Examples for surface resistive EM manipulating materials includes Statitec™ of 20 ohm/sq or 1000 ohm/sq EMF Inc. and metallic materials, for example a metal foil. Resistive EM manipulating materials may be combined with near field magnetic RF shielding materials. In some embodiments the garment may comprise materials for absorbing electromagnetic radiation, as disclosed in PCT/IL2011/050003 filed Nov. 3, 2011, which is incorporated herein by reference in entirety.

Additional examples include materials capable of diverting, reflecting disrupting and/or attenuating EM propagation such that EM energy may be released away from the body of the wearer and/or be caused to propagate away from an undesired area within the garment.

Optionally, the EM manipulating materials includes materials which absorb electric fields and/or magnetic fields. Optionally the complex permittivity of such EM manipulating materials at a frequency of about 1 Ghz, $\in'$ is between 2 and 60 or around 8-30 and $\in''$ is between 1 and 30 or even 5-10 and regarding the complex permeability of the absorbing material, $\mu'$ is between 1 and 30 or about 20 and $\mu''$ is between 1 and 30 or even 6 to 15. The absorbing material may be Eccosorb® MCS, GDS and BSR, which the specifications thereof are incorporated herein by reference. Optionally, the thickness of the one or more layers and/or patches formed from of EM manipulating materials is between about 0.1 millimeters (mm) and about 20 mm.

Optionally, area between the EM transducer positions in the garment is covered with the EM manipulating materials. Alternatively, one or more patches of EM manipulating materials separate between the EM transducer positions, for example by gaps of between about 1 cm and about 5 cm for EM energy within the frequency range of between 0.5 GHz and 4 GHz and/or with predetermined impedance discontinuities manipulates EM energy propagation. The gaps may allow a part of the EM energy to escape from the garment and not only be absorbed by the EM manipulating materials.

Gaps may also reduce the hazard of conducting energy from one EM transducer position to another. Direct conductance between the EM transducer positions via unintended pathways may thus be reduced and/or prevented.

Optionally, area between the EM transducer positions is designed to attenuate and/or deflect stray energies, optionally by taking advantage of impedance differences.

This may have gaps dimensioned to facilitate escape of energy from the garment and/or to reduce the hazard of conducting energy from one EM transducer position to another. This area may be in the circumference of EM transducer positions and/or along the short path between EM transducer positions.

Figure 5:
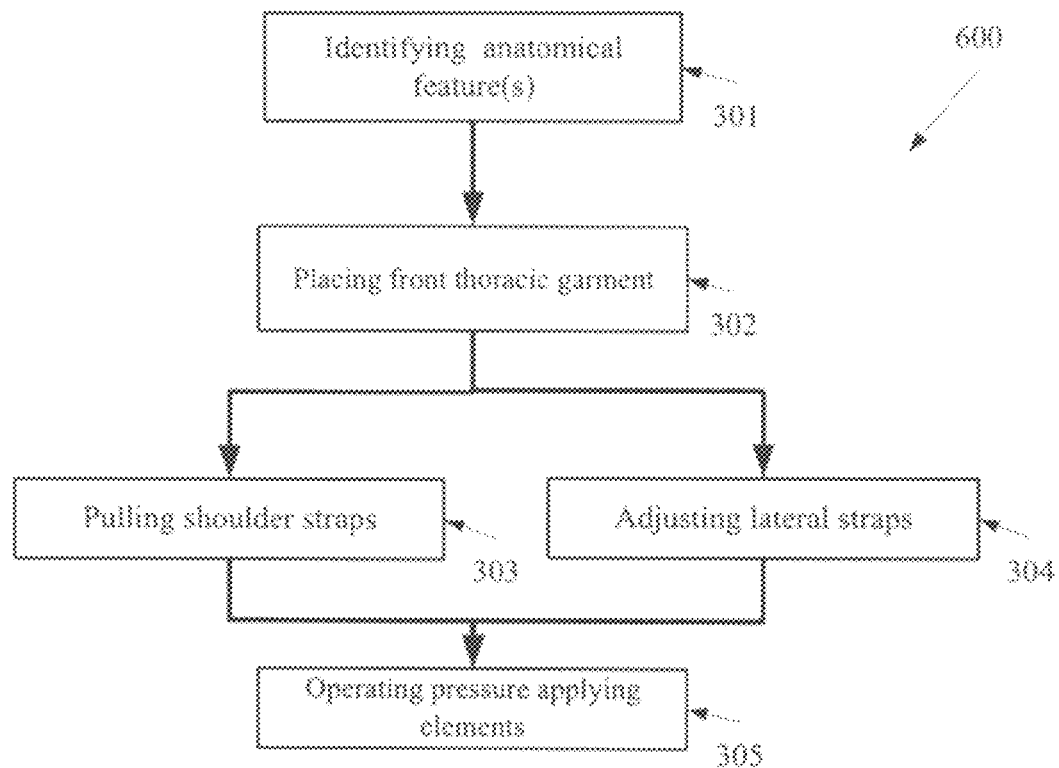
FIG. 5 is a flowchart of an exemplary preliminary fitting session, according to some embodiments of the present invention.

Reference is now made to FIG. 5, which is a flowchart 600 of an exemplary preliminary fitting session, according to some embodiments of the present invention.

First, as shown at 301, instructions identifying one or more anatomical features are provided. The anatomical features are optionally marked on a wearer body, for example on thoracic skin surface areas, for instance the below the bottom tip of the jugular notch of the wearer. These anatomical feature(s) are optionally defined by a fitting protocol defining a distance from a certain organ or bodily anatomical feature, for example a thoracic skin surface area, characterized as a skeletal feature, such as the jugular notch or any anatomical feature on the body.

Now, as shown at 302, the wearer is instructed to place the front thoracic garment piece of the thoracic garment 130 is placed against or close to his chest such that the positioning marker 142, for example the handhold 145 is located in a predefined orientation or position in relation to the anatomical feature(s). This placement is performed while the wearer holds the handhold 145. The alignment of the positioning marker 142 of the thoracic garment 130 in relation to the anatomic feature(s) aligns the EM transducer units associated with the front thoracic garment piece (if any) with one or more anterior anatomical tissues on the chest of the wearer. This placement includes laying the shoulder straps 151 on the shoulders of the wearer such that the front thoracic garment piece 140 is in front of the chest of the wearer and the back thoracic garment piece 141 is in front of the back of the wearer.

Now, as shown at 303, the wearer is instructed to adjust the shoulder straps 151, 152 and optionally additional straps, optionally by a single pulling maneuver as recited above. The single pulling maneuver optionally symmetrically and simultaneously shortens the length of segments of the shoulder straps 151, 152 between the front and back thoracic garment piece 140, 141. In such a manner, the alignment of the left and right sides of each of front and back thoracic garment piece 140 is maintained.

Optionally, the pulling of the straps fixates their length, for instance in an irreversible manner. As described above, such fixating is facilitated by a flexible pawl which supports continuous motion of each of the shoulder straps 151, 152 in one direction while preventing motion of the respective strap in the opposite direction.

Optionally, a separate locking action may be taking after one or more of the adjustment actions. For example, activating a locking mechanism, such as turning of a screw, inserting a pin, knot or releasing a knob, pressing and crimping the strap(s) in place to allow rewearing the garment 130 without adjustment.

As described above, one or both of the straps 151, 152 are detachably connected straps. In such embodiments, one or both of the straps 151, 152 may be removed after being used for adjustment. In such a manner, in use the worn garment has 1 strap or none, providing more comfort to the wearer and has a more limited visibility.

Optionally, as shown at 304, the wearer is instructed to adjust and optionally to fixate lateral straps, for example as described above, either temporarily or permanently.

As shown at 305, pressure applying elements of the EM transducer units 133 may now be operated to bring EM transducers to contact with the skin of the wearer and/or with clothing worn by the wearer. This may be done manually or automatically.

Now, after the thoracic garment piece 140 is worn, one or more intrabody thoracic tissues can be monitored by analysis of the outputs of the EM transducers of the EM transducer units. Above instructions may be provided, optionally in real time, by a presentation unit such as a display or a speaker of a computing unit and/or by a manual or a guide.

The analysis of the output of the EM transducer(s) may be used to identify a dielectric related property or a change of the dielectric related property of one or more thoracic tissues of the wearer, optionally in real time. As used herein, a dielectric related property of a specific volume which includes one or more organs and/or tissues may describe or relate to an interaction with EM energy and may be represented by a frequency dependent complex number describing the electrical permittivity and/or material conductivity. For example, dielectric related property may be an electric permittivity coefficient, conductivity coefficient and/or a magnetic permeability coefficient of a material, optionally composite, within a specific volume. Such a dielectric related property may be affected for example by a presence or distribution of fluid, concentration of substances, such as salts, glucose, in the fluid in the internal tissue and/or organ, the ratio of fibrotic tissue, a concentration of inflammatory substance in the fluid in the internal tissue and/or organ and physical configuration of organs or tissues of different properties in the volume measured.

Measurements of dielectric related properties may be conducted by transmitting EM energy and/or EM signal and/or intercepting it using the EM transducer unit(s) 133.

Intercepted EM energy and derived electrical signals may be analyzed using one or more signal properties using known signal analysis methods. For example time domain or frequency domain analysis methods, for example one or more of amplitude, phase, and signal morphology feature extraction, and/or group delay analyzed over different bands of frequencies (potentially between 100 MHZ and 5 GHz or any portion thereof). Other sensors may be used, such as ECG sensors, impedance, and acoustic.

It is expected that during the life of this patent many relevant methods and garments will be developed and the scope of the term a sensor, a transducer and a fastener is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A thoracic garment for bringing an EM transducer to contact with a thoracic surface area of a wearer, comprising:
    a front thoracic garment piece and a back thoracic garment piece at least one of said front and back thoracic garment pieces having at least one EM transducer or at least one mechanical connector for connecting said at least one EM transducer, said front thoracic garment piece having an arrangement of passages formed therein or thereon;
    a handhold mechanically connected to said front thoracic garment piece;
    a positioning marker located on or in said front thoracic garment piece such that when said thoracic garment is worn by a human wearer and said front thoracic garment piece is placed against or close to the chest of said human wearer, said positioning marker located in a predefined position in relation to one or more anatomical features of the wearer;
    a plurality of straps each threaded in said arrangement of passages;
    wherein said thoracic garment is configured to be adapted by said wearer using a first hand to hold said handhold for holding said front thoracic garment piece against or close to said chest such that said positioning marker is positioned at said predefined position while using a second hand for pulling said plurality of straps.

2. The thoracic garment of claim 1, further comprising at least one brake unit to lock the movement of each of said plurality of straps.

3. The thoracic garment of claim 1, further comprising at least one pulling element associated with each of said plurality of straps and adapted to be pulled by said second hand for pulling said plurality of straps said plurality of.

4. The thoracic garment of claim 3, wherein said arrangement of passages is symmetrically arranged in or on said front thoracic garment piece so that said at least one pulling element is configured to pull symmetrically said plurality of straps along the left and right sides of said human wearer.

5. The thoracic garment of claim 1, wherein said positioning marker is integrated with said handhold.

6. The thoracic garment of claim 1, wherein when the garment is configured to be adapted by said wearer said handhold is located in a midway between armpits and below the bottom tip of the anatomical feature.

7. The thoracic garment of claim 1, wherein said anatomical feature is the jugular notch of said human wearer.

8. The thoracic garment of claim 1, wherein said front thoracic garment piece comprises a non-stretchable breast plate.

9. The thoracic garment of claim 8, wherein said breast plate has said at least one EM transducer mounted thereon or therein.

10. The thoracic garment of claim 1, wherein said back thoracic garment piece comprises a non-stretchable back plate mechanically connected to at least some of said plurality of straps.

11. The thoracic garment of claim 1, wherein at least one of said front and back thoracic garment pieces has at least one mechanical connector for at least one EM transducer configured to detachably connect to said at least one EM transducer.

12. The thoracic garment of claim 11, wherein each of the back thoracic garment piece and the front thoracic garment piece has an EM transducer or a mechanical connector for an EM transducer formed thereon.

13. The thoracic garment of claim 1, wherein the back thoracic piece is mechanically connected to at least some of said plurality of straps, and wherein each of said plurality of straps passes in a mechanical communication with a pawl which allows continuous motion of a respective said strap in one direction while preventing motion in at least the opposite direction.

14. The thoracic garment of claim 13, wherein said plurality of straps comprises shoulder straps which mechanically connect between said back thoracic garment piece and said front thoracic garment piece and mounted such that when said thoracic garment is worn by said human wearer and said front thoracic garment piece is placed against or close to the chest of said human wearer, said shoulder straps are laid over the left and right shoulders of said human wearer.

15. The thoracic garment of claim 1, wherein said plurality of straps are adapted to be pulled to bring said thoracic garment back piece to a predetermined distance from the cervical vertebra C7 (vertebra prominens) of the wearer.

16. The thoracic garment of claim 15, wherein said plurality of straps are adapted to be pulled to bring said thoracic garment back piece to a neckline position when a movement stopping structure is positioned in contact with the cervical vertebra C7 (vertebra prominens) of the wearer.

17. The thoracic garment of claim 16, wherein the movement stopping structure prevents a movement of one of said plurality of straps when the EM transducer or mechanical connector for an EM transducer is positioned at a predetermined location with respect to a body part or organ of the wearer.

18. The thoracic garment of claim 1, further comprising left and right lateral straps each mechanically connected to said back thoracic garment piece and connected to said front thoracic garment piece such that when said thoracic garment is worn by said human wearer and said front thoracic garment piece is placed against or close to the chest of said human wearer, said left and right lateral straps are adapted to be laid over the underarm region of said human wearer.

19. The thoracic garment of claim 1, wherein said arrangement of passages comprises an arrangement of channels.

20. The thoracic garment of claim 1, comprising a pressure applying element associated with said thoracic garment for applying a pressure at least on the EM transducer when said thoracic garment is worn by said human wearer so that said EM transducer applies a respective pressure on a thoracic skin surface area of said wearer.

\* \* \* \* \*